United States Patent
Haralampu

(10) Patent No.: US 9,182,372 B2
(45) Date of Patent: Nov. 10, 2015

(54) STOPPED-FLOW, MICRO-FLUIDIC DEVICE AND METHOD FOR THE CHARGE-BASED SEPARATION OF COMPLEX ANALYTE MIXTURES

(71) Applicant: Stephen G. Haralampu, Belmont, MA (US)

(72) Inventor: Stephen G. Haralampu, Belmont, MA (US)

(*) Notice: Subject to any disclaimer, the term of this patent is extended or adjusted under 35 U.S.C. 154(b) by 215 days.

(21) Appl. No.: 13/682,430

(22) Filed: Nov. 20, 2012

(65) Prior Publication Data

US 2013/0153422 A1    Jun. 20, 2013

Related U.S. Application Data

(60) Provisional application No. 61/562,924, filed on Nov. 22, 2011.

(51) Int. Cl.
  *G01N 27/447* (2006.01)
  *B81B 1/00* (2006.01)
  *B01L 3/00* (2006.01)

(52) U.S. Cl.
  CPC ............ *G01N 27/44795* (2013.01); *B81B 1/00* (2013.01); *B01L 3/502753* (2013.01)

(58) Field of Classification Search
  CPC .......... G01N 27/447; G01N 27/44717; G01N 27/4473; G01N 27/47739; G01N 27/47756; G01N 27/44759; G01N 27/44791; G01N 27/44795
  USPC .......... 204/450, 451, 454, 548, 600, 601, 644
  See application file for complete search history.

(56) References Cited

U.S. PATENT DOCUMENTS

| | | | |
|---|---|---|---|
| 4,362,612 A | 12/1982 | Bier | |
| 4,465,582 A | 8/1984 | Richman | |
| 4,971,670 A | 11/1990 | Faupel et al. | |
| 5,275,706 A | 1/1994 | Weber | |

(Continued)

FOREIGN PATENT DOCUMENTS

| WO | WO 2008/006201 | 1/2008 |
|---|---|---|
| WO | WO 2013/078236 | 5/2013 |

OTHER PUBLICATIONS

M. Becker, et al. "Separation of proteins using a novel two-depth miniaturized free-flow electrophoresis device with multiple outlet fractionation channels" Journal of Chromatography A, vol. 1216, 2009, p. 8265-8269.*

(Continued)

*Primary Examiner* — J. Christopher Ball
(74) *Attorney, Agent, or Firm* — Lisa M. Warren, Esq.; Morse, Barnes-Brown & Pendleton, P.C.

(57) ABSTRACT

The present inventions relate to micro-fluidic devices and related methods of fractionating samples of analytes, such as peptides or proteins, according to their isoelectric points. The disclosed micro-fluidic devices and related methods provide a fractionation sufficient to enhance the performance of immunochemistry and/or tandem liquid chromatography-mass spectrometry workflows. Such methods and devices are capable of fractionating complex samples in a short time, using a small amount of sample, do not require high voltages and are further characterized by their high degree of reproducibility and ease of use.

24 Claims, 11 Drawing Sheets

(56) References Cited

U.S. PATENT DOCUMENTS

| | | | |
|---|---|---|---|
| 5,447,612 | A | 9/1995 | Bier et al. |
| 6,328,868 | B1 | 12/2001 | Weber |
| 6,638,408 | B1 | 10/2003 | Speicher et al. |
| 7,351,376 | B1 | 4/2008 | Quake et al. |
| 7,615,354 | B2 | 11/2009 | Faupel et al. |
| 7,622,081 | B2 | 11/2009 | Chou et al. |
| 7,655,477 | B1 | 2/2010 | Schneider et al. |
| 7,931,791 | B2 | 4/2011 | Tolley et al. |
| 2007/0235335 | A1 | 10/2007 | Strand et al. |
| 2008/0035484 | A1 | 2/2008 | Wu et al. |
| 2009/0188795 | A1 | 7/2009 | Oakey et al. |
| 2009/0291507 | A1 | 11/2009 | Clemmens et al. |
| 2010/0155243 | A1 | 6/2010 | Schneider et al. |
| 2010/0252435 | A1 | 10/2010 | Weber |
| 2011/0256574 | A1 | 10/2011 | Zhang et al. |

OTHER PUBLICATIONS

D. Janasek, et al. "Isotachophoresis in free-flow using a miniaturized device" Analytical Chemistry, vol. 78, No. 11, Jun. 2006, p. 3815-3819.*

International Search Report for International Application PCT/US2012/066120, dated Mar. 21, 2013.

S. Köhler, et al., "PDMS free-flow electrophoresis chips with integrated partitioning bars for bubble segregation", Lab Chip, 11, 309-314 (2011).

Ros, et al., "Protein purification by Off-Gell electrophoresis", Proteomics 2(2): 151-156 (2002).

Michel, et al., "Protein fractionation in a multicompartment device using Off-Gel™ isoelectric focusing", Electrophoresis 24, 3-11 (2003).

* cited by examiner

*Uniform widths of outlet ports 2*

*Variable depths of outlet ports 2*

STOPPED-FLOW, MICRO-FLUIDIC DEVICE AND METHOD FOR THE CHARGE-BASED SEPARATION OF COMPLEX ANALYTE MIXTURES

RELATED APPLICATION

This application claims the benefit of U.S. Provisional Application Ser. No. 61/562,924, filed Nov. 22, 2011, the entire teachings of which are incorporated herein by reference.

BACKGROUND

Protein research is the mainstay for understanding the machinery of biological systems. Recently, proteomics research and protein biomarker research have made a strong impact in furthering our knowledge of biological systems, and holds great promise for research into diseases, hopefully leading to useful drug treatments and diagnostics.

Traditionally, electrophoresis has been a key laboratory technique for separating and studying proteins, and has been used as an analytical technique itself. SDS-PAGE (sodium dodecyl sulfate-polyacrylamide gel electrophoresis) was one of the earliest electrophoretic methods for separating complex protein mixtures according to their molecular weight. Isoelectric focusing is another electrophoretic technique that separates mixtures according to their charge. A very powerful separation technique is 2-dimensional (2D) electrophoresis, in which the mixture is first fractionated by isoelectric focusing in a gel strip, and then the strip is equilibrated with SDS, mated with a polyacrylamide slab gel, and the charge separated mixture is further separated according to molecular weight, creating a 2-dimensional image of the mixture with charge separation in the x-direction and molecular weight separation in the y-direction. The result of a 2D procedure is a spot image, and further analysis needs to be done on these spots for actual protein identification. Two approaches are antibody probing methods, like western blotting, or amino acid sequencing.

Recently, mass spectrometry (MS) has become a very important tool for identifying proteins by sequence. Total mass, and fragment masses are used to deduce the amino acid sequence, and hence protein identity. Most recently, as the capabilities of the MS instrumentation have improved, the MS has increasingly been taking the place of the second dimension of 2-D electrophoresis. Tandem liquid chromatography-mass spectrometry (LC-MS) is the workhorse of protein identification today. The LC fractionates samples by hydrophobicity, and the MS identifies the proteins associated with the fractions. Samples analyzed by LC-MS can be more complex as instrumentation improves, analyzing up to hundreds of proteins per sample. However, typical biological samples contain thousands of proteins. Thus, some fractionation prior to LC-MS analysis is still required in the sample preparation workflow. Charge-based separations are considered to be important, because of the additional structural information that can be deduced from charge.

The methods used to prepare complex protein or peptide samples for subsequent immunoassay or LC-MS analyses were generally developed as analytical tools themselves. Consequently, they have high separation resolution, tend to be complex to run, and are usually expensive on a per sample basis. With advancements in, for example LC-MS, only crude fractionation is necessary in the preparative steps, and with the proliferation of high throughput workflows there is a need for effective, rapid, low-cost, charge-based fractionation. Also, it is advantageous to have the analytes separated in a gel-free system to minimize losses, and to simplify sample clean-up prior to any LC-MS procedure.

Strong cation exchange chromatography is a charge-based protein sample fractionation technique. This has the advantage that chromatography equipment is prevalent in the laboratory environment, and it is easily automated. It suffers the disadvantage that many of the analyte species irreversibly bind to the column, which limits the quantitative capabilities of the method. Isoelectric focusing is the other charge-based separation process frequently used in the biochemistry laboratory.

Electrophoretic separations dominate charge-based separation methods. Isoelectric focusing is done in a pH gradient. Charged molecules migrate in an electric field within the gradient where the overall charge of an amphoteric molecule is affected by pH. An amphoteric molecule gains positive charges at pH values below the $pK_a$s of the charged moieties within the molecule, hence migrates toward the cathode, or attains negative charges at higher pH values, hence migrates toward the anode. At some intermediate pH, positive and negative charges balance and there is no net movement in the electric field, the isoelectric point (pI). In isoelectric separation, a complex mixture is separated into bands along a pH gradient corresponding to each component's isoelectric point. The pH gradients are established in two basic ways: (1) with carrier ampholytes, a complex mixture of amphoteric molecules line up in the electric field to give a piecewise discrete pH gradient; and (2) immobilized pH gradients fabricated into a polyacrylamide gel by incorporating acrylamido buffers, monomers with acids or bases pendant on the side chains, which locally buffer a specific pH. Frequently, a combined approach is used.

The most typical configuration for isoelectric focusing is the IPG strip (immobilized pH gradient). This format requires relatively large sample volumes (10-50 µg), long running times (5 to 24 hours), and high applied voltage (1,000-10,000 Volts). This method has exquisitely fine separation resolution to about 0.01 pH units, and has been used as an analytical tool in protein research. The separated mixture is in a gel matrix, however, and needs to be recovered and cleaned prior to any subsequent analysis, such as LC-MS. This is usually accomplished by running an SDS-PAGE second dimension. Protein spots in the 2D-SDS-PAGE need to be excised, cleaned of SDS and eluted prior to LC-MS analysis. Non-specific adsorption of protein to the polyacrylamide matrix, and the workflow complexity of recovering the separated proteins to a liquid phase make a gel-free separation technique desirable. Additionally, the high applied voltage poses a safety hazard, and the power supplied to these systems causes them to heat, which may damage proteins or peptides, and requires active cooling.

Capillary isoelectric focusing (CIEF) is a newer technology conducting the separation in a capillary using carrier ampholytes to create the pH gradient, usually in a gel-free medium. CIEF utilizes very small sample sizes on the order of 1 µL. Proteins or peptides may be recovered by pushing the separated mixture out of the capillary along the direction of the separation. This is not easily accomplished, because the capillary ends are in contact with the anode and cathode buffer pools. So, the capillary must be disconnected from the electrophoresis running system and attached to a mechanical pumping system to recover the contents of the capillary. Usually, however, the analytes are visualized in place using fluorescent tags.

In WO 2008/006201 a CIEF device is taught wherein the analytes can be removed from the capillary via a single cross-flow channel. This geometry requires a complex fluid handling system to hydraulically position a segment of the separated analyte over the cross-flow extraction zone prior to the application of an extraction pressure to recover only that separated segment. The flow characteristics of such a device are designed so that it is impossible to simultaneously and uniformly recover all of the separated segments.

U.S. Pat. No. 7,655,477 B1 teaches a CIEF system with a multiplicity of side channels that recover separated analytes. This device requires a series of buffers of different ionic strengths to coordinate flow through the device, and the device does not intend to recover the samples for subsequent downstream analysis. Instead, UV-Visible spectra are obtained for the separated analytes within the side channels. It would be difficult to physically recover analytes because all of the movement is accomplished by electrophoretic or electroosmotic movement, and the analytes would be lost to the electrode buffer or oxidized at the electrode itself.

Free-flow electrophoresis (U.S. Pat. Nos. 5,275,706 and 6,328,868) is another gel-free separation method intended for the purification of large samples. Being gel-free is an advantage for certain protein or peptide workflows prior to subsequent immunoassay or mass spectrometry analysis. Free-flow electrophoresis (FFE) has not been well adopted because the equipment is cumbersome to use and expensive to purchase. As a continuous flow method, the equipment is difficult to set up, balance and calibrate. Furthermore, it requires a large sample volume (0.1-10 mg usually at concentrations on the order of 1 mg/mL). The method greatly shortens run times to 0.5-1 hours, and requires about 2,000 Volts to accomplish the separation at a resolution of about 0.1 pH units.

Micro FFE (µFFE) devices have been reported (e.g., S. Köhler, C. Weilbeer, S. Howitz, H. Becker, V. Beuhausen and D. Belder, *PDMS free-flow electrophoresis chips with integrated partitioning bars for bubble segregation*, in Lab on a Chip, 2011, 11:181). Although these address the FFE drawbacks of sample size and high voltage (about 100 V), they retain the fluidic complexity of FFE, requiring the flow rates of multiple inlet and outlet ports to be balanced.

There are numerous refinements of the FFE concept. See for example, U.S. Patent Application 2010/0252435 A1 and U.S. Pat. No. 6,328,868. These refine the FFE concept with additional flows to balance the system to deal with electroosmotic flow, operational variations, or with buffer systems that refine the pH gradient, but do not address the operational complexity or equipment expense of running FFE.

Multi-compartment electrolyzers (MCE) are large-scale isoelectric separation devices. These are comprised of liquid compartments separated by permeable membranes that allow the analyte molecules to migrate from compartment to compartment. The pH in each compartment is controlled by charged membranes (for example U.S. Pat. No. 4,971,670), and/or by various components in the buffer systems (for example U.S. Pat. Nos. 4,362,612 and 6,638,408). The initial intent was for purifying large quantities of peptides or proteins for non-MS uses. Consequently, these systems tend to be too large for analytical sample preparation. The MCE format is useful for fractionating complex samples prior to LC-MS because the fractionated material can be recovered in a gel-free, liquid phase. MCEs suffer the drawback of needing large samples (many milligrams), and generally need many hours to run, and have only crude pH resolution of about 0.1-1.0 pH units. An additional disadvantage is that proteins and peptides frequently adhere to the membranes and are lost.

Yet another approach is the Offgel™ system (Proteomics 2002, 2, 151-156 and Electrophoresis 2003, 24, 3-11) manufactured by Agilent Technologies (Santa Clara, Calif.). This is essentially an MCE wherein a linear array of open-bottomed chambers is placed on top of an IPG strip. The pH of each chamber is controlled by the average pH of the IPG segment over which it lies, and the membrane between each chamber is the IPG segment beneath the wall between two adjacent chambers. This is a very effective system for fractionating complex samples to a pI resolution of about 0.3 pH units. The fractions are recovered in liquid for relatively direct incorporation into an LC-MS workflow. The Offgel system still requires large samples, less than the traditional MCE, but more than a typical IPG strip. Long separation times (12-24 hours) and high voltages (up to 10,000 Volts) are additional disadvantages.

Ampholyte-free separations are advantageous for certain downstream analytical methods, such as mass spectrometry, since ampholytes interfere with protein and peptide mass spectra. U.S. Pat. Nos. 5,447,612 and 7,615,354 B2 and U.S. Pat. Appl. 2010/0252435 A1 all suggest similar buffer systems based on mixtures of organic acids and bases.

There is a need in the protein and peptide workflows, such as LC-MS, for a technology that can fractionate a complex sample in a short time, on the order of 1 hour; can provide charge information; can use a small sample, less than about 10 µg; does not require high voltages, preferably less than 200 Volts; has a high reproducibility; and is easy to use.

SUMMARY

There is a need for a device and method for fractionating analytes suitable in LC-MS works flows with short operation times, high capacity for sample complexity, and low operational voltages. The present invention is directed toward solutions to address these and other needs, in addition to having other desirable characteristics that will be appreciated by one of skill in the art upon reading the present specification.

A micro-fluidic device capable of fractionating a complex peptide or protein mixture is disclosed. A protein or peptide analyte sample, along with appropriate pH gradient generating components, is flowed into a chamber and then the flow is stopped. An electric field applied to the complex analyte sample and pH generating components perpendicular to the flow direction causing a pH gradient to form and for the analytes to migrate to the pH where they have no net electrophoretic mobility (their pI). Once fractionated, flow is re-initiated and the analyte fractions are recovered through multiple ports. It can be useful in the design of the chamber and ports that the flow in the separation chamber is laminar, to minimize any re-mixing of the fractions. Fractions are suitable for subsequent analysis by, for example, immunoassay methods or LC-MS.

The advantage of the disclosed embodiments is that they can provide a fractionation sufficient to enhance the performance of immunochemistry and/or LC-MS workflows in a device that is inexpensive, simple and can be manufactured as a disposable product. As a microfluidic device, sample sizes can be kept small, run times kept short, and low applied voltage make the separation safer to run.

In certain embodiments, a micro-fluidic device for fractionating a sample of analytes according to their isoelectric points can include a micro-fluidic chamber comprising one or more walls and a separation chamber zone contained within the one or more walls. An inlet port can be situated at a first end of the micro-fluidic chamber for introducing a sample of analytes into the separation chamber zone. A plurality of outlet ports can be situated beyond a second end of the micro-fluidic chamber, and the second end can be substantially opposite the first end. The plurality of outlet ports can extend across a width that is equal to at least part of a width (e.g., only a portion of a width, in certain embodiments) of the separation chamber zone. A plurality of channels each can lead from a different widthwise position in the separation chamber zone to one of the plurality of outlet ports. One or more flow path deflector elements can be situated proximate the inlet port. The one or more flow path deflector elements further can be situated between the inlet port and the plurality of outlet ports. The one or more flow path deflector elements can be situated in one or more positions that precede (e.g., are upstream of) the separation chamber zone. The one or more flow path deflector elements can be situated between the inlet port and the separation chamber zone. At least one of the one or more flow path deflector elements can block a shortest path between the inlet port and at least one of the plurality of outlet ports. For instance, the one or more flow path deflector elements each can have a position.

The at least one of the one or more flow path deflector elements further blocks a shortest path between the inlet port and each of the plurality of outlet ports. The one or more flow path deflector elements can include one or more of a cylindrical column, a foil shaped member, a triangular prism, a v-shaped column, a rectangular prism, a thicket, or other flow path deflector elements. Accordingly, combinations of these and other flow path deflector elements can be included. The one or more flow path deflector elements can include a plurality of flow path deflector elements that extend across a width that is equal to at least part of the width of the separation chamber zone. The one or more flow path deflector elements can be positioned in such a way as to prevent substantial lateral intermixing of a plurality of fractionated analyte groups as the plurality of fractionated analyte groups flow from one or more positions in the separation chamber zone (which is located beyond the flow path deflector elements) to the plurality of channels.

For at least one of the plurality of channels, there is a pair of substantially opposing walls leading to the at least one of the plurality of channels, wherein the pair of substantially opposing walls narrows in a direction leading to the at least one of the plurality of channels. In some embodiments, for each channel of the plurality of channels, there is a pair of substantially opposing walls leading to the channel, wherein the pair of substantially opposing walls of each channel narrows in a direction leading to the channel. In some embodiments, for each channel of the plurality of channels, there are two or more walls included in the device that form a bottleneck in a direction leading from the separation chamber zone to the channel.

A plurality of buffer components can be situated in the separation chamber zone in such a way as to enable a pH gradient to form within the separation chamber zone in the presence of an electric field. An electric field generation device (or components thereof) can be included in the device and/or can be configured to generate an electric field having a direction extending across the width of the separation chamber zone.

The one or more flow path deflector elements can include a plurality of flow path deflector elements extending across a width that is equal to at least part of the width of the separation chamber zone. The plurality of flow path deflector elements, the plurality of channels, or both can be spaced apart at non-uniform distances. A density of the plurality of flow path deflector elements can increase (e.g., in a quadratic fashion) moving from a widthwise position aligned with either edge of the width of the separation chamber zone to a widthwise position aligned with a center of the width of the separation chamber zone. A density of the plurality of channels can decrease (e.g., in a quadratic fashion) moving from a widthwise position aligned with either edge of the width of the separation chamber zone to a widthwise position aligned with a center of the width of the separation chamber zone. The one or more flow path deflector elements can include an initial flow path deflector element and a plurality of additional flow path deflector elements. The initial flow path deflector element can be situated between the inlet port and the plurality of additional flow path deflector elements. The plurality of additional flow path deflector elements can be situated between the initial flow path deflector element and the plurality of outlet ports. The initial flow path deflector element can block a shortest path between the inlet port and the plurality of outlet ports. The plurality of additional flow path deflector elements can be situated in a row. Each of the plurality of channels can be substantially parallel to each other.

The plurality of channels can have widths that decrease moving from a widthwise position aligned with either edge of a width of the separation chamber zone to a widthwise position aligned with a center of the width of the separation chamber zone. Alternatively or additionally, the plurality of outlet ports can have areas that decrease moving from a widthwise position aligned with either edge of a width of the separation chamber zone to a widthwise position aligned with a center of the width of the separation chamber zone. For example, the plurality of outlet ports can have variable depths, variable widths, or both, where the variation in the depths, widths, or both is sufficient to provide variation in overall area. Accordingly, outlet ports and/or channels situated at widthwise positions nearer to a center of a width of the separation chamber zone can be more restrictive of flow than outlet ports and/or channels situated farther from the center of the width of the separation chamber zone. A first channel of the plurality of channels leading from a widthwise position in a center portion of the separation chamber zone can have a width that is smaller than a width of a second channel of the plurality of channels leading from a different widthwise position in an edge portion of the separation chamber zone. Widths of the plurality of channels can increase as a function of widthwise position relative to a center of a width of the separation chamber zone. The function with which the widths of the plurality of channels increase can be a quadratic function.

In certain embodiments, a method for isoelectrically fractionating a sample of analytes can include introducing the sample into a separation chamber zone through an inlet port situated on a first end of the micro-fluidic chamber. The sample can be caused to flow through part of the separation chamber zone and to impact one or more flow path deflector elements situated proximate the inlet port and situated between the inlet port and a plurality of outlet ports. At least one of the one or more flow path deflector elements can block a shortest path between the inlet port and at least one of the plurality of outlet ports, whereby the sample can be redirected upon impacting the one or more path deflector elements. Flow of the sample can be halted while the sample is in the separation chamber zone. The halted sample can be isoelectrically fractionated into a plurality of fractionated analyte groups. The plurality of fractionated analyte groups can be caused to flow through a remainder of the separation chamber zone and through a plurality of channels each leading from a different widthwise position in the separation chamber zone to one of the plurality of outlet ports. The plurality of fractionated analyte groups can be caused to flow through the plurality of outlet ports, and the plurality of outlet ports can be situated beyond a second end of the micro-fluidic chamber. The second end of the micro-fluidic chamber can be substantially opposite the first end of the micro-fluidic chamber.

In certain further embodiments, the plurality of fractionated analyte groups do not substantially laterally intermix as the plurality of fractionated analyte groups flow from the separation chamber zone to the plurality of channels. The step of causing the plurality of fractionated analyte groups to flow through a remainder of the separation chamber zone and through a plurality of channels further can include causing the plurality of fractionated analyte groups to flow past a plurality of pairs of substantially opposing walls each leading to one of the plurality of channels. Each of the plurality of pairs of substantially opposing walls can narrow in a direction leading to the plurality of channels.

The one or more deflector elements can include one or more of a cylindrical column, a foil shaped member, a triangular prism, a v-shaped column, a rectangular prism, or a thicket. Each of the plurality of outlet ports can pass one or more of the plurality of fractionated analyte groups. Each of the plurality of fractionated analyte groups can have a different range of isoelectric points. The ranges of isoelectric points of the plurality of fractionated analyte groups can be overlapping or non-overlapping. Each of the plurality of channels can be substantially parallel to each other. The sample of analytes can include a leading portion that includes non-analyte material, an analyte portion that includes the analytes, and a trailing portion that includes non-analyte material.

The step of causing the sample to impact one or more flow path deflector elements can include causing the sample to impact an initial flow path deflector element and a plurality of additional flow path deflector elements. The initial flow path deflector element can be situated between the inlet port and the plurality of additional flow path deflector elements, and the plurality of additional flow path deflector elements can be situated between the initial flow path deflector element and the plurality of outlet ports. The initial flow path deflector element can block a shortest path between the inlet port and the plurality of outlet ports.

The plurality of channels through which the plurality of analyte groups are caused to flow can have widths that decrease moving from a widthwise position aligned with either edge of a width of the separation chamber zone to a widthwise position aligned with a center of the width of the separation chamber zone. A first channel of the plurality of channels leading from a widthwise position in a center portion of the separation chamber zone can have a width that is smaller than a width of a second channel of the plurality of channels leading from a different widthwise position in an edge portion of the separation chamber zone. Widths of the plurality of channels can increase as a function of widthwise position relative to a center of a width of the separation chamber zone. The function with which the widths of the plurality of channels increase can be a quadratic function.

In certain embodiments, a micro-fluidic device for fractionating a sample of analytes according to their isoelectric points includes a micro-fluidic chamber comprising one or more walls, a separation chamber zone contained within the one or more walls, and a fluid distribution chamber zone situated in such a way as to precede the separation chamber zone. An inlet port can be situated at a first end of the micro-fluidic chamber for passing a sample of analytes into the separation chamber zone. A plurality of outlet ports can be situated beyond a second end of the micro-fluidic chamber substantially opposite the first end. The plurality of outlet ports can extend across a width that is equal to at least part of a width of the separation chamber zone. A plurality of channels each can lead from a different widthwise position in the separation chamber zone to one of the plurality of outlet ports. A first flow path redirection element can be situated in the fluid distribution chamber zone proximate the inlet port and situated between the inlet port and the plurality of outlet ports. The first flow path redirection element can block a shortest path between the inlet port and at least one of the plurality of outlet ports. A plurality of additional flow path redirection elements can be situated in the fluid distribution chamber zone proximate the first flow path redirection element and further can be situated between the first flow path redirection element and the plurality of outlet ports. The first flow path redirection element and the plurality of additional flow path redirection elements can be positioned in such a way as to substantially prevent lateral intermixing of a sample of analytes flowing through the separation chamber zone and out of the plurality of outlet ports.

In certain embodiments, a micro-fluidic device for fractionating a sample of analytes according to their isoelectric points includes a pipette coupled to a micro-fluidic chamber comprising one or more walls and a separation chamber zone contained within the one or more walls. An inlet port can be situated at a first end of the micro-fluidic chamber for introducing a sample of analytes from the pipette into the separation chamber zone. A plurality of outlet ports can be situated at a second end of the micro-fluidic chamber substantially opposite the first end, and the plurality of outlet ports can extend across a width that is equal to at least part of a width of the separation chamber zone. A plurality of channels each can lead from a different widthwise position in the separation chamber zone to one of the plurality of outlet ports. One or more flow path deflector elements can be situated proximate the inlet port and situated between the inlet port and the plurality of outlet ports. At least one of the one or more flow path deflector elements can block a shortest path between the inlet port and at least one of the plurality of outlet ports.

In certain embodiments, a method for isoelectrically fractionating a sample of analytes includes causing a sample to flow through a plurality of first ports situated on a first end of a micro-fluidic chamber and into a separation chamber zone contained within the micro-fluidic chamber by applying a negative pressure at a second port situated at a second end of the micro-fluidic chamber that is substantially opposite the first end. In this manner, the sample can be caused to flow in a first direction. Flow of the sample can be halted once the sample is evenly distributed in the separation chamber zone and isoelectrically fractionating the halted sample into a plurality of fractionated analyte groups. The plurality of fractionated analyte groups can be caused to flow through the separation chamber zone and out the plurality of first ports. In this manner, the plurality of fractionated analyte groups can be caused to flow in a second direction substantially opposite the first direction.

The flow of the sample can be halted once the sample is evenly distributed in and fills all or some of the separation chamber zone. The step of causing a sample to flow through the plurality of first ports further can include causing the sample to flow through the plurality of first ports and through a plurality of channels each leading from one of the plurality of first ports to a different widthwise position in the separation chamber zone. The step of causing the plurality of fractionated analyte groups to flow through the separation chamber zone and out the plurality of first ports further can include pressurizing a fluid distribution chamber zone situated between the second port and the separation chamber zone. The step of pressurizing the fluid distribution chamber zone further can include causing a fluid to flow through the inlet port and into the fluid distribution chamber zone. The fluid can have a viscosity that is less than a viscosity of any of the plurality of fractionated analyte groups.

The above-discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

DETAILED DESCRIPTION

Figure 1:
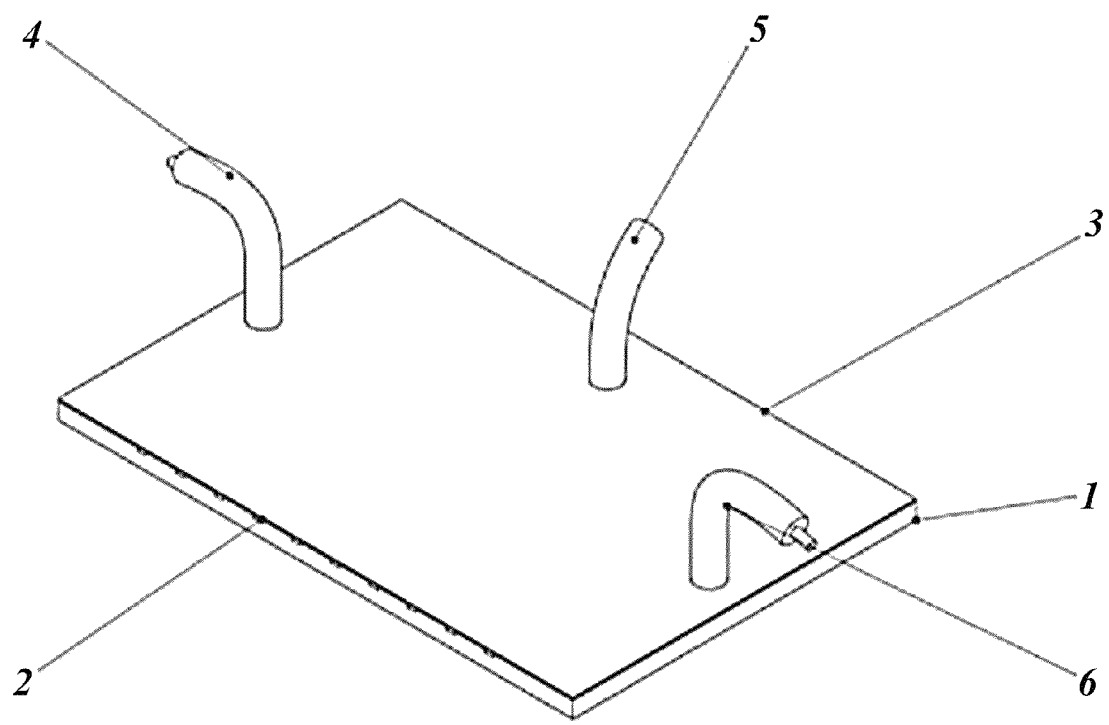
FIG. 1 depicts a perspective view of a micro-fluidic device according to certain embodiments.

The disclosed embodiments provide a micro-fluidic device capable of fractionating a complex mixture of analytes, such as peptides or proteins, within a separation chamber zone according to their isoelectric points. The fractionated mixture is recovered as discrete fractions uniformly ejected from the separation chamber zone perpendicular to a direction in which the analytes move during fractionation, herein referred to as a "direction of separation." This is enabled at least in part by including one or more flow path deflector elements situated proximate an inlet port and further being situated in such a way as to be between the inlet port and a plurality of outlet ports. For instance, the one or more flow path deflector elements can block a shortest path between the inlet port and at least one of the plurality of outlet ports. Upon the sample impacting the one or more flow path deflector elements, the sample can be redirected in a particular manner, such as a predetermined manner that enables the sample to flow in such a way that is substantially absent any lateral intermixing (e.g., of fractionated analyte groups, once separation has occurred).

In yet further embodiments, the one or more flow path deflector elements can block a shortest path between the inlet port and all of the plurality of outlet ports. The outlet ports can be preceded by (e.g., can be downstream of) a plurality of channels. The channels can be substantially parallel to each other, and each can lead from a different widthwise position in the separation chamber zone to one of the plurality of outlet ports. Each channel can be preceded by (e.g., downstream of) a pair of walls that narrows in a direction leading to the channel, e.g., thereby forming a bottleneck shape. Furthermore, the separation chamber zone of the device is preferably less than 1 mL in volume, more preferably less than 500 µL and most preferably less than 250 µL. Accordingly, the device provided in embodiments herein can be utilized for small but complex samples requiring low operational voltage.

FIGS. 1 through 10, wherein like parts are designated by like reference numerals throughout, illustrate example embodiments of a micro-fluidic device. Although certain embodiments will be described with reference to the example embodiments illustrated in the figures, it should be understood that many alternative forms can be embodied. One of skill in the art will appreciate different ways to alter the parameters of the embodiments disclosed, such as the size, shape, or type of elements or materials, in a manner still in keeping with the spirit and scope of the devices provided in the disclosure herein.

Figure 2:
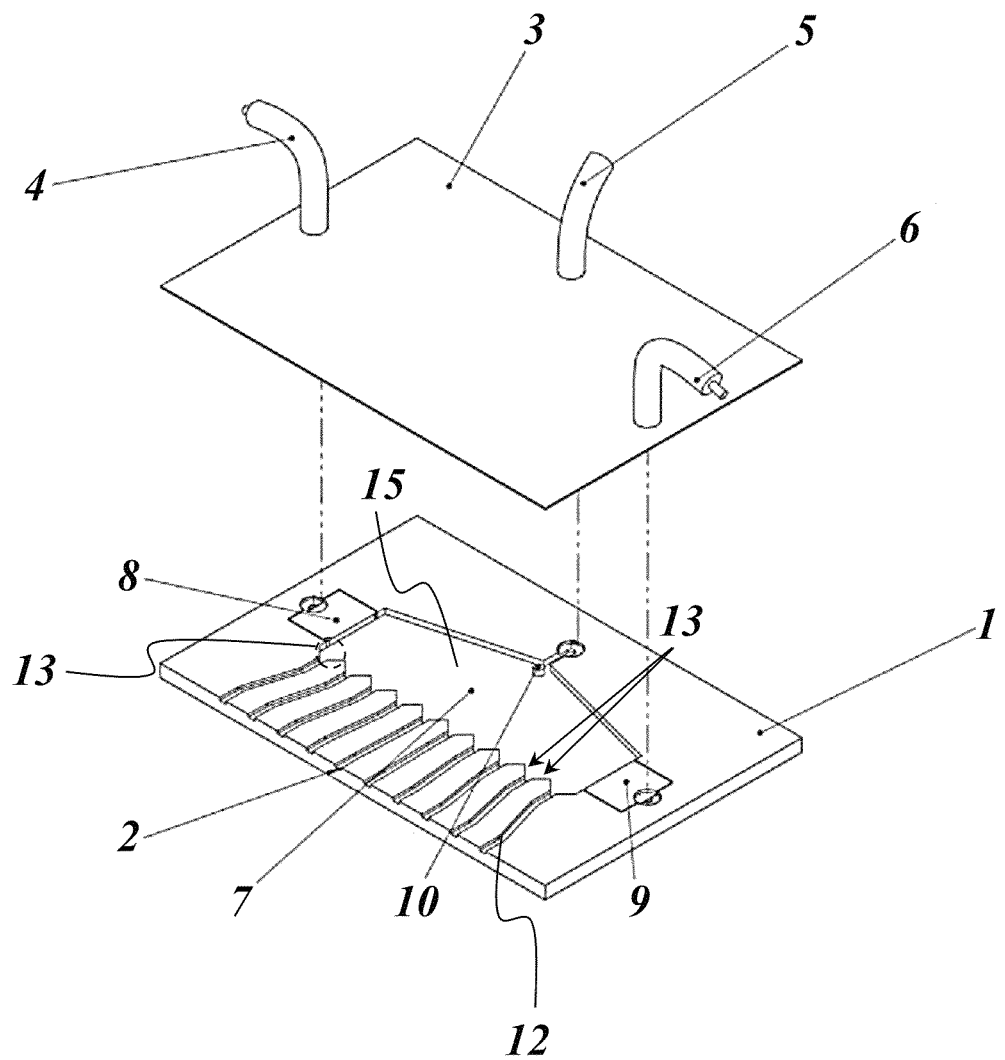
FIG. 2 depicts an exploded view of the micro-fluidic device of FIG. 1.

FIGS. 1 and 2 depict one embodiment of the device, comprised of a micro-fluidic chamber 1 and lid 3 that is sealed to the chamber as to create a separation chamber zone 7, a single inlet port 5 and multiple channels 12 (e.g., formed of a piping, tube, housing, sets of opposing walls, etc.) each leading to (e.g., terminating at) an outlet port 2 (e.g., an opening, slit, hole, gap, orifice, etc.) forming an exit to one of the channels 12. The micro-fluidic chamber 1 is less than 50 mm in length, and preferably less than 20 mm in length. The inlet port 5 is provided, e.g., through the lid. A sample of analytes is introduced and flowed into the device via the inlet port. Alternatively, analyte may be aspirated into the device by applying a negative pressure at the inlet port and drawing the sample in through the outlet ports.

The micro-fluidic chamber 1 includes a plurality of different and preferably distinct portions, which can be designated as various chamber zones. Accordingly, the device contains the separation chamber zone 7, as well as a fluid distribution chamber zone 15. The fluid distribution chamber zone 15 can be situated between the separation chamber zone 7 and the inlet port 5, and the separation chamber zone 7 can be situated between fluid distribution chamber zone 15 and the channels 12, e.g., such that the fluid distribution chamber zone 15, the separation chamber zone 7, the channels 12, and the outlet ports 2 are arranged sequentially in a series of portions in fluid communication. Accordingly, in illustrative embodiments, the fluid distribution chamber zone 15 precedes (e.g., is upstream of) the separation chamber zone 7.

One or more flow path deflector elements (such as an initial flow path deflector element 10 and a plurality of additional flow path deflector elements 11) can be situated in the fluid distribution chamber zone 15, and can "smooth" the fluid flow as it transitions from the inlet port to the separation chamber zone 7, e.g., by causing redirection of impinging analytes in such a way that produces laminar, substantially parallel flow of the analytes within the separation chamber zone 7. In illustrative embodiments, the plurality of additional flow path deflector elements 11 are included and situated in such a way as to be between the initial flow path deflector element 10 and a plurality of outlet ports 2 (see FIG. 3). For instance, the plurality of additional flow path deflector elements 11 can be aligned in a row, and can be spaced at uniform or non-uniform distances from one another. Accordingly, the flow path deflector elements 10, 11 can assist in discharging the sample from the device in a uniform manner subsequent to fractionation. In other embodiments, only a single flow path deflector element (e.g., the initial flow path deflector element 10) is included. In still other embodiments, only the plurality of flow path deflector elements 11 is included. One of skill in the art will appreciate a wide variety of ways to arrange the one or more flow path deflector elements (e.g., 10, 11) in such a way as to create substantially parallel flow of a sample of analytes through the separation chamber zone 7.

Once the sample of analytes has flowed as far as (e.g., has flowed into, but not beyond) the separation chamber zone 7, flow is preferably stopped. The sample of analytes is then fractionated in the separation chamber zone 7 between two electrode pads (8 and 9), which are connected to a direct current power supply via contacts 4, 6. One of skill in the art will appreciate other ways to create an electric field having a direction extending across a width of the separation chamber zone 7. Accordingly, in the presence of such an electric field generated by the depicted or an alternative electric field generation device, the sample of analytes fractionates into a plurality of fractionated analyte groups.

Accordingly, it should be appreciated that the separation chamber zone 7 is the particular area in which the sample of analytes is intended to be fractionated. Thus, in illustrative embodiments, the separation chamber zone 7 does not include any flow path deflector elements 10, 11, but rather is formed of an open area in which analytes of a sample can flow and separate according to isoelectric points under the presence of a generated electric field. Thus, in illustrative embodiments provided herein, the separation chamber zone 7 can be defined as the open space situated between the channels 12 and the flow path deflector elements 10, 11. In such illustrative embodiments, the flow path deflector elements 10, 11 are included in a fluid distribution chamber zone 15 contained within the micro-fluidic chamber 1 (see FIGS. 2, 3, and 6) which precedes (e.g., is upstream of) the separation chamber zone 7. In further illustrative embodiments, the fluid distribution chamber zone 15 is generally triangular shape. However, other shapes are possible and contemplated by the present disclosure.

In general, the flow path deflector elements 10, 11 can be any structural mechanism for determining or defining the flow path of a sample, as determined by impact of the sample against the flow path deflector elements 10, 11. For instance, the flow path deflector elements 10, 11 can be cylindrical columns, walls forming defined pathways, or any other suitable deflector element.

Once sufficiently fractionated (e.g., in an amount suitable for the intended usages of the sample), the fractionated analyte groups are pushed out of the device through the plurality of outlet ports 2 by re-initiating flow through the inlet port. In illustrative embodiments, prior to passing through the plurality of outlet ports 2, the fractionated analyte groups additionally pass through a plurality of channels 12, each of which leads from a different widthwise position in the separation chamber zone 7 to one of the plurality of outlet ports 2. In illustrative embodiments, all of the plurality of channels 12 are substantially parallel to one another. However, in alternative embodiments, only some or none of the plurality of channels 12 are parallel to one another. In yet further illustrative embodiments, preceding (e.g., upstream of) at least one of the channels 12 is a pair of substantially opposing walls 13 that narrow in a direction leading to the channel 12. In this manner, the pair of substantially opposing walls 13 can form a bottleneck shape that compacts (e.g., compresses, condenses, intermixes, etc.) flow of one or more fractionated analyte groups flowing into the channel 12. In illustrative embodiments, such a pair of walls 13 precedes (e.g., is upstream of) each of the plurality of channels 12, so as to form a plurality of pairs of substantially opposing and narrowing walls 13.

In illustrative embodiments, the analyte sample is mixed with buffer components that allow a pH gradient to form in an electric field to effect the isoelectric separation. The analyte is loaded into the device through the inlet port 5 by any suitable mechanical method, such as a micro-pump, syringe or pipette. Once sample has flowed as far as the separation chamber zone 7 (e.g., has flowed into but not beyond), flow of the sample of analytes is preferably stopped. To minimize the amount of sample used, introduction into the separation chamber zone 7 can be accomplished by sandwiching the analyte between a leading, sample-free running buffer, and a trailing sample-free buffer. Thus, analyte is substantially only present within the separation chamber zone 7. A DC electric field is applied across the electrodes 4, 6, allowing a pH gradient to form, and for the proteins or peptides analytes to align in the electric field according to their pI. Once fractionation is completed, the electric field is optionally turned off, flow is reinitiated through the inlet port 5, and the fractionated analyte in the separation chamber zone 7 is forced via parallel flow through the multiplicity of outlet ports 2. The flow path deflector elements 10, the additional flow path deflector elements 11, and the cross-sectional areas of the outlet ports 2 can be sized, shaped, and positioned in such a way to assure the substantially uniform and substantially parallel flow from the separation chamber zone 7 into the channels 12 and through the outlet ports 2, e.g., thereby preventing substantially lateral intermixing of fractionated analyte groups within the separation chamber zone 7.

Figure 3:
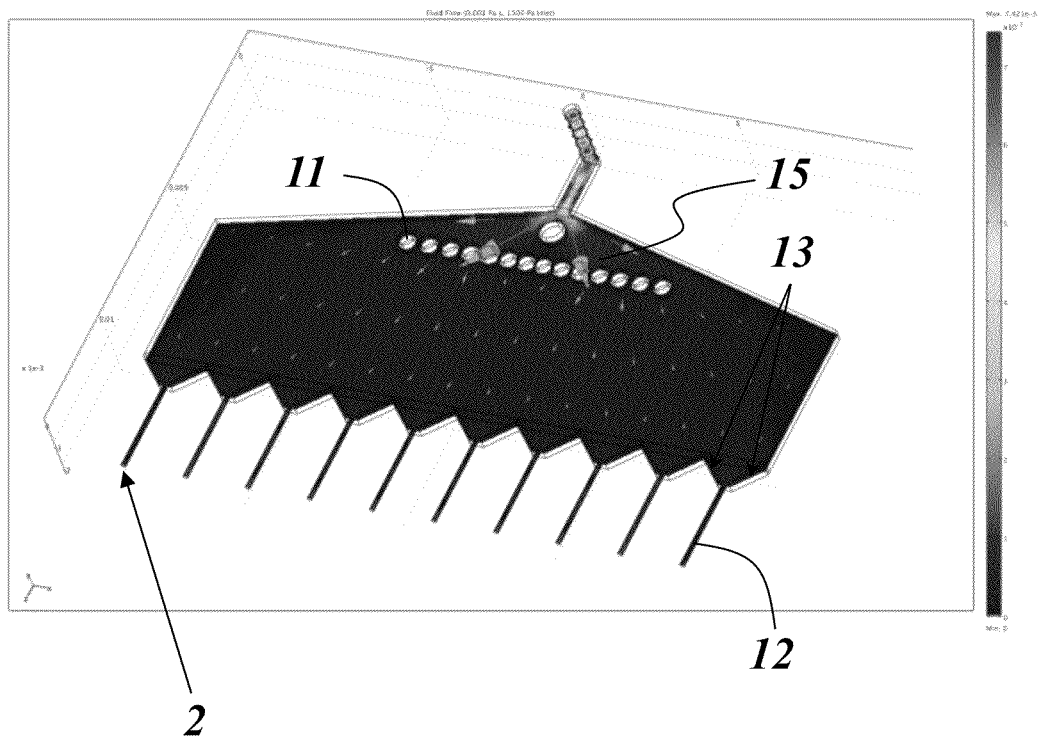
FIG. 3 depicts analysis of the flow pattern through the device in which the flow of various fractionated analyte groups is substantially parallel, thereby minimizing re-mixing of the fractionated sample.

FIG. 3 depicts a fluid flow analysis through the device for a Newtonian fluid, showing that flow is substantially parallel as the fractionated analyte groups are forced from the separation chamber zone 7 through the channels 12 (depicted by the parallel nature and relatively uniform length of the flow arrows in the separation chamber). As described previously herein, the substantially parallel flow through the separation chamber zone 7 and in the channels 12 can prevent lateral intermixing of the fractionated analyte groups. For ease of collection, the outlet ports 2 can be spaced in accordance with common, multiple-sample receiving vessels, such as 96, 384 or 1536 well plate formats or any of various MALDI target plate configurations. Alternatively, the fractionated analyte can be blotted directly onto a membrane and probed with antibodies. An advantage of the device's small size is that it is amenable to valuable samples as well as not introducing a large sample dilution factor that is common with other separation methods. The simple construction of the device makes it suitable for single use applications, such as high throughput analysis.

The principles for the charge-based separation are the same as those known for isoelectric focusing. Proteins or peptides are typically separated in an electric field in a pH gradient by migrating in the electric field until they reach the pH of their neutral charge, and migration ceases. Most commonly, the separation is done in a polyacrylamide gel with the aid of mobile carrier ampholytes, immobilized acrylamido buffers, or both to create the pH gradient. Since the device of the current invention is gel-free, the buffer systems used here need to support the formation of a suitable pH gradient in the electric field. This can be done using carrier ampholytes, or mixtures of amphoteric buffers, such as Good's buffers (see for example U.S. Pat. No. 5,447,612). It can be appreciated that the shape of the resultant pH profile is dependent upon the concentrations and number of components in the separation buffer. In peptide separations, for a relatively concentrated analyte, since the peptides themselves are amphoteric, they can behave like carrier ampholytes and support the creation of a pH gradient without the addition of many other buffer compounds. The choice of buffer components is affected by both the pH range required for the separation, and by the compatibility requirements of any downstream sample preparation, such as for mass spectrometry.

The endpoints of the pH gradient established in the separation chamber can be affected by using immobilized acrylamido buffer polymers in the gel buffer pads 8, 9 at the electrodes 4, 6, as is known in the art of making IPG strips.

Another important feature of the invention is that the hydraulic flow through the device is substantially parallel through the separation chamber to the outlet ports so that fractionated proteins or peptides can be recovered with minimal subsequent re-mixing. A flow analysis is shown in FIG. 3 for a Newtonian buffer, which represents a worst case for potential re-mixing. In some embodiments, the flow path deflector elements 10, 11 are designed such that the resulting pressure drop between the inlet distribution zone and the separation chamber promotes parallel flow in the separation chamber zone 7. Additionally, it might also be advantageous to add a polymer, or other component, that mitigates mixing by adding a yield stress to the buffer rheology. A yield stress in the buffer fluid's rheology would have the effect of further promoting the parallel flow nature within the separation chamber zone 7. A suitable component for this purpose is linear polyacrylamide, but other uncharged, water soluble polymers are adequate, such as polyethylene glycol and polysaccharides including, but not limited to, hydroxypropyl methylcellulose, methylcellulose, or agarose. Further, a mixture of linear acrylamido buffer polymers can serve the dual function of providing modified rheological properties and ability to establish a pH gradient in the electric field.

Accordingly, this micro-fluidic chamber 1 can be designed such that flow in the separation chamber zone 7 between the inlet port 5 and the multiple outlet ports 2 is substantially parallel. The fluid distribution chamber zone 15 (e.g., forming an initial entry zone) that includes flow path deflector elements 10, 11 similarly can evenly distribute the buffer flow throughout the separation chamber zone 7. It can be equally desirable to form the outlet ports 2 and/or channels 12 so as to promote substantially parallel flow pattern in the separation chamber zone 7. The lengths and widths of the multiple channels 12 can be individually designed so that the flow across the separation zone is uniform, i.e., the pressure distribution within the separation chamber zone 7 is maintained relatively uniform. For convenience, it is desirable to have the outlet ports 2 in register with some common collection device such as a 96-well or 384-well plate.

Since the micro-fluidic chamber 1 can be small as compared to traditional IEF devices, separation times are shorter, and the required voltage to affect fractionation is lower. Since the micro-fluidic chamber 1 can be about 20 mm, and typical IPG strips are 70 to 110 mm in length, the applied voltages can be 15-30% the applied voltages of a typical IPG application. This represents a significant reduction in required operating voltage. Furthermore, given that the separation zone is gel-free, it is expected that the analyte components have electrophoretic mobilities 100 to 1000 greater than in typical IPG applications. Therefore, the device provided herein provides benefits, such as reduced separation times and lower applied voltages.

The device provided herein can be fabricated from any suitable material as is known in the art for micro-fluidic devices. A common material is silicon, which additionally can have the properties of electrically insulating and conductive regions that would facilitate the design and introduction of the anode and cathode electrodes. Silicon also has good thermal conduction properties, so such a device could easily be cooled during the fractionation process. Alternatively, polymeric materials such as polycarbonate or polydimethylsiloxane, or glass are also useful.

Figure 4:
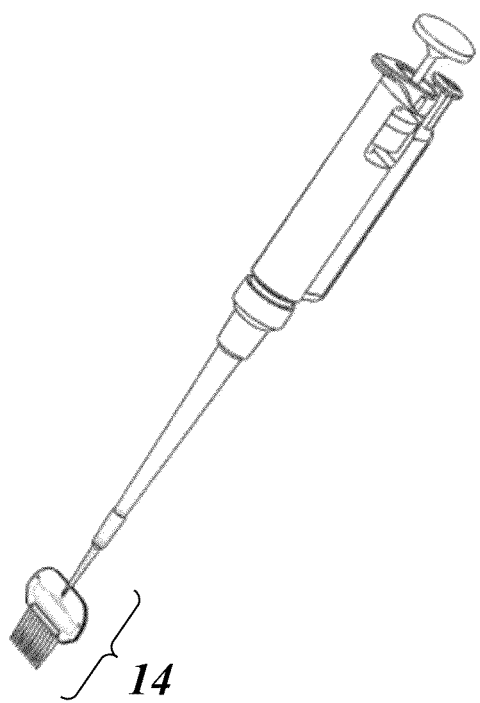
FIG. 4 depicts an embodiment of the micro-fluidic device affixed to a pipette, instead of a complex array of pumps as would be used in FFE.
Figure 5:
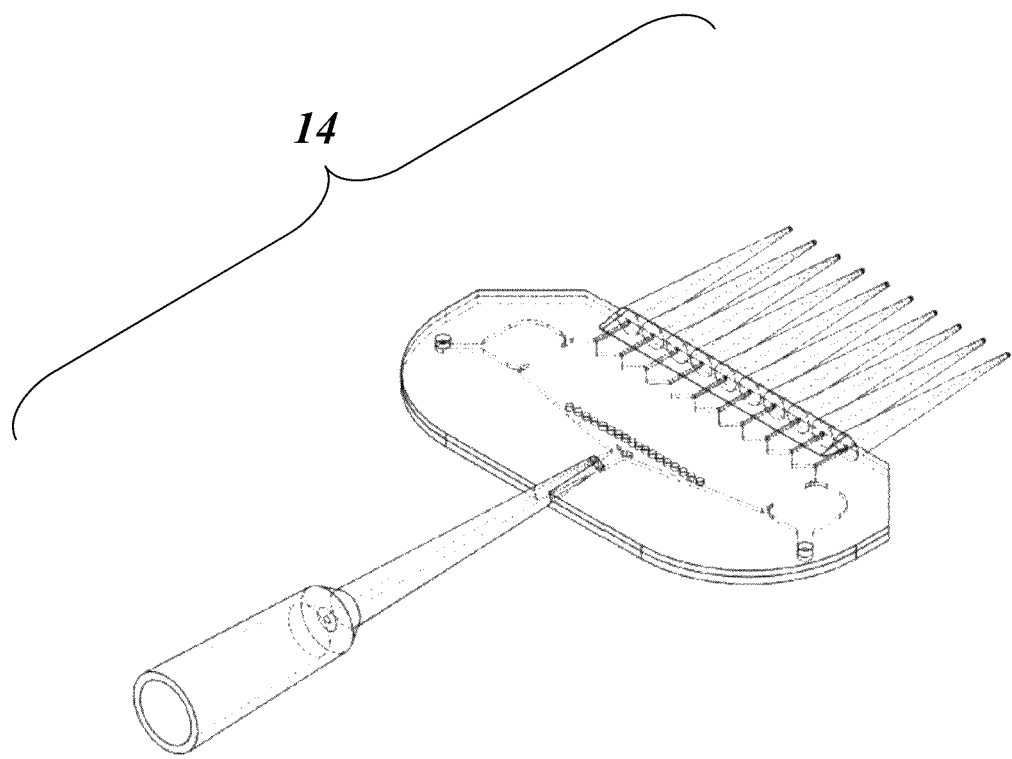
FIG. 5 depicts a close up perspective view of the micro-fluidic chamber of the micro-fluidic device of FIG. 4.

The device disclosed herein is suitable for charge-based separations sufficient to enhance the performance of downstream analytical techniques, such as immunoassays and mass spectrometry. Complex inlet and outlet pumping schemes are not required and thus can be excluded from certain embodiments, since the flow path deflector elements 10, 11 are positioned in such a way as to cause the flow to be sufficiently uniform in the separation zone to prevent re-mixing of the separated analytes. Consequently, the device can be loaded and unloaded using a laboratory pipette or another micro-pumping device, such as a syringe. For instance, FIGS. 4 and 5 depict the micro-fluidic device as an attachment to a standard laboratory pipette. The outlet ports are designed to coincide with the spacing of a 384-well plate for convenient recovery of the separated analytes. Unseparated sample can be aspirated into the separation chamber with the pipette, drawing the sample through the multiplicity of outlet ports. Once the fractionation is complete, the separated analytes are pushed out again through the outlet ports by the pipette.

Figure 6:
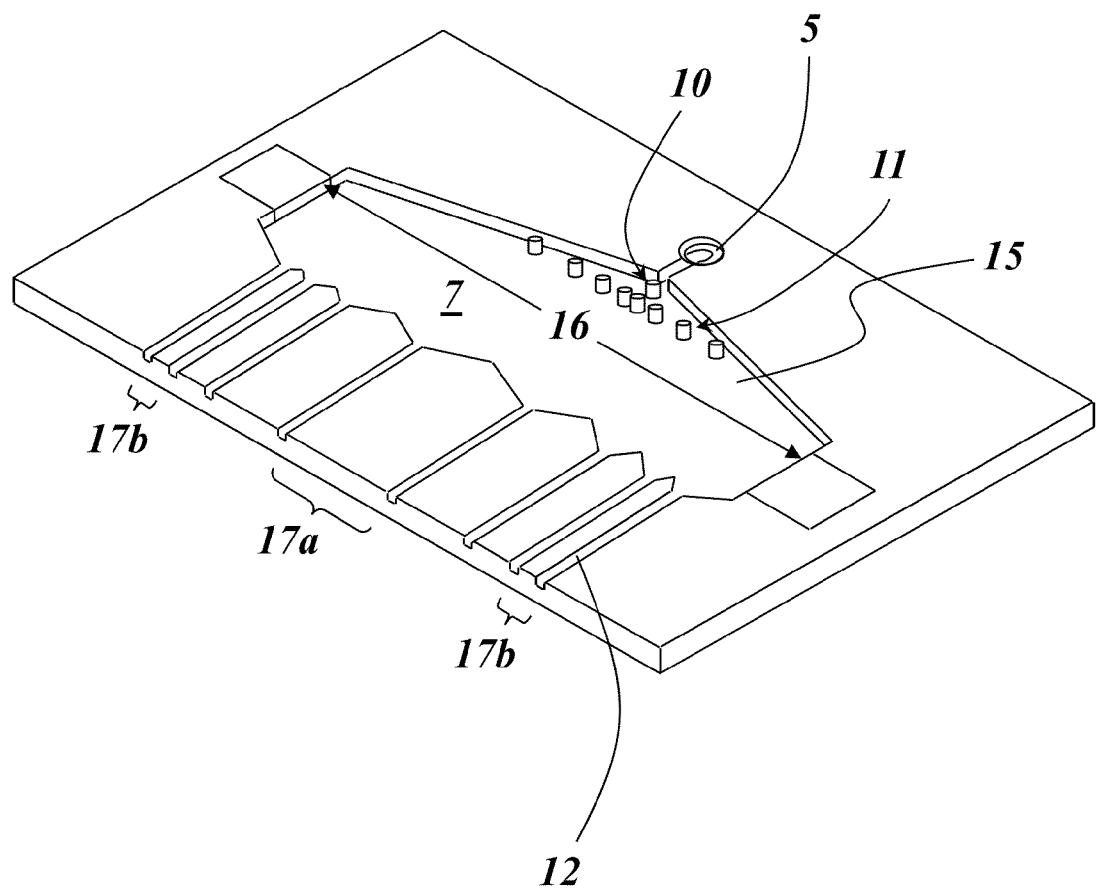
FIG. 6 depicts a perspective view of a plurality of flow path deflector elements and a plurality of channels included in the micro-fluidic chamber having non-uniform density (e.g., distributions)

FIG. 6 depicts a further example embodiment, in which the channels 12 are positioned in such a way that a density of the channels 12 (e.g., a "channel distribution density") increases when moving from a widthwise position aligned with an edge of a width 16 of the separation chamber zone 7 to a widthwise position aligned with a center of the width 16 of the separation chamber zone 7. For instance, the density of the channels 12 at a widthwise position in the micro-fluidic chamber 1 that is proximate a center of the width 16 of the separation chamber zone 7 can be lesser than a density of the channels 12 at a widthwise position in the micro-fluidic chamber 1 that is proximate either edge of the width 16 of the separation chamber zone 7. Furthermore, the density of the channels 12 can be a function of widthwise position that decreases when moving from a widthwise position aligned with either edge of the width 16 of the separation chamber zone 7 to a widthwise position aligned with the center of the width 16 of the separation chamber zone 7. Accordingly, distances (e.g., distance 17a) between channels 12 situated nearer to the center of the width 16 of the separation chamber zone 7 can be lesser than distances (e.g., distances 17b) between channels 12 situated nearer to the edges of the width 16 of the separation chamber zone 7.

Furthermore, flow path deflector elements (e.g., the plurality of flow path deflector elements 11) that are included in the device can be arranged with a center-increasing distribution density. For example, a density of the flow path deflector elements 11 (e.g., a "flow path distribution density") can increase when moving from a widthwise position aligned with an edge of the width 16 of the separation chamber zone 7 to a widthwise position aligned with the center of the width 16 of the separation chamber zone 7. For instance, the density of the flow path deflector elements 11 at a widthwise position in the micro-fluidic chamber 1 that is proximate a center of the width 16 of the separation chamber zone 7 can be greater than a density of the flow path deflector elements 11 at a widthwise position in the micro-fluidic chamber 1 that is proximate either edge of the width 16 of the separation chamber zone 7. Furthermore, the density of the flow path deflector elements 11 can be a function of widthwise position that increases (e.g., in a quadratic fashion) when moving from a widthwise position aligned with either edge of the width 16 of the separation chamber zone 7 to a widthwise position aligned with the center of the width 16 of the separation chamber zone 7. Accordingly, distances between flow path deflector elements 11 situated nearer to the center of the width 16 of the separation chamber zone 7 can be greater than distances between flow path deflector elements 11 situated nearer to the edges of the width 16 of the separation chamber zone 7.

Utilizing such distribution densities of the flow path deflector elements (e.g., 10, 11) and/or the channels 12 can be beneficial in some instances for promoting substantially parallel flow of sample through the separation chamber zone 7. For instance, by providing narrower gaps between the flow path deflector elements (e.g., 10, 11) and/or the channels 12, flow of sample can be restricted at positions where the pressure of the fluid is highest. This can cause buildup of sample at the high pressure, narrow passages, thereby causing lateral redirection of the sample, thus promoting distribution of the sample throughout the separation chamber zone 7 and further promoting parallel flow through the separation chamber zone 7.

It should be noted that the number of flow path deflector elements 11 can be equal or unequal to the number of channels 12 included in the device. Furthermore, the distribution density of the channels 12 can be proportional or un-proportional to the distribution density of the flow path deflector elements 11. Thus, the non-uniform distances between the channels 12 can be proportional or un-proportional to the non-uniform distances between the flow path deflector elements 11.

Figure 7:
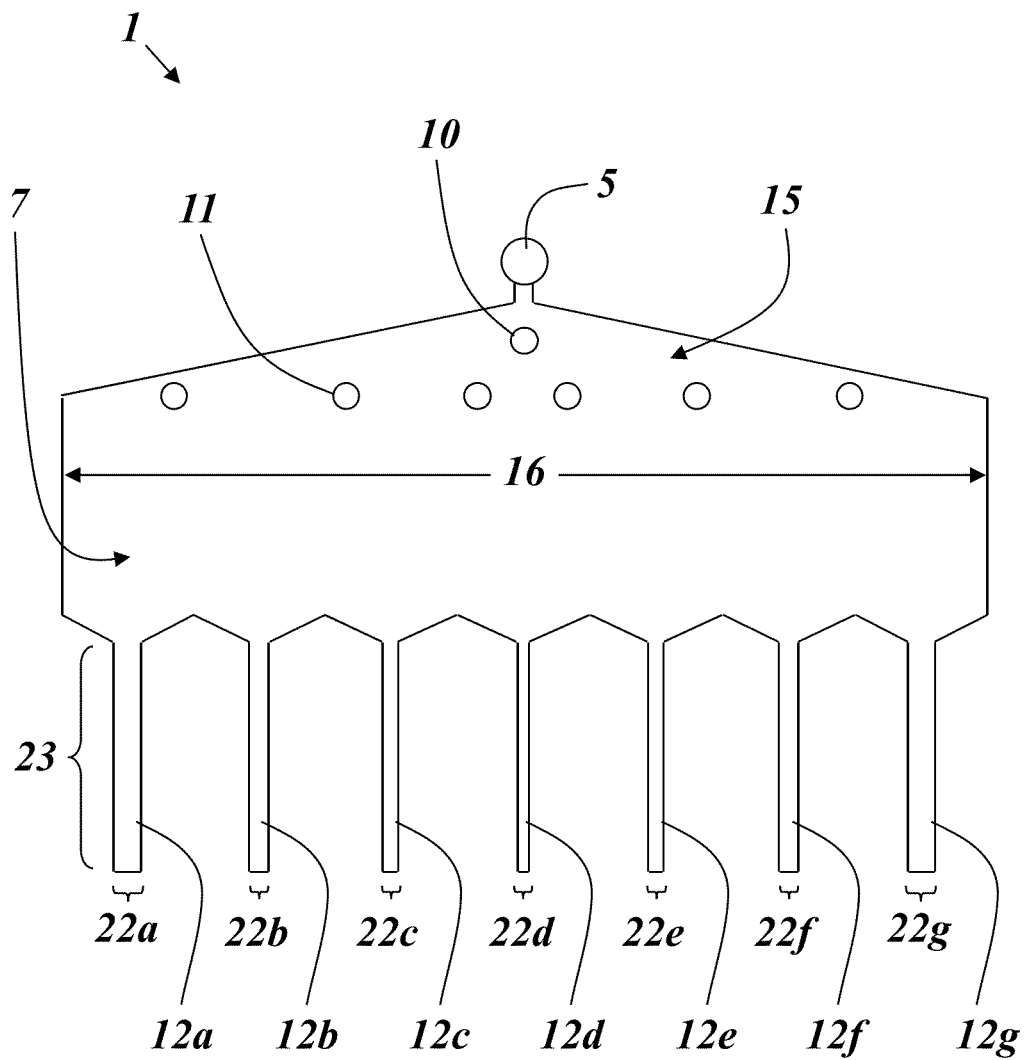
FIG. 7 depicts a top view of a micro-fluidic chamber of a micro-fluidic device having a plurality of channels having non-uniform widths.

Additionally or alternatively to having (a) a non-uniform distribution density of the flow path deflector elements 10, 11 and/or (b) a non-uniform distribution density of the channels 12, widths of the channels 12 can be non-uniform. For instance, FIG. 7 depicts an example embodiment in which seven channels 12a-g have widths 22a-g. In the example embodiment of FIG. 7, channels 12a-g leading from a widthwise position in the separation chamber 7 that is relatively nearer to a center of the width 16 thereof are narrower than channels 12a-g leading from a widthwise position that is relatively farther from the center of the width 16. Accordingly, the widths 22a, 22g can be greater than the widths 22b, 22f; the widths 22b, 22f can be greater than the widths 22c, 22e; the widths 22c, 22e can be greater than the width 22d. In this manner, widths 22a-g of the channels 12a-g can decrease moving from either edge of the width 16 of the separation chamber zone 7. This can be effective, for instance, in restricting flow of fractionated analyte groups through the middle portion (i.e., at the center of the width 16) of the separation chamber zone 7, thereby restricting flow of the fractionated analyte groups at positions where pressure is higher. This, in turn, can promote uniform flow rates through all of the channels 12a-g, thereby assisting in creating substantially parallel flow of the fractionated analyte groups through the separation chamber zone 7. In illustrative embodiments, the widths 22 of the plurality of channels 12 increase as a function of widthwise position relative to a center of the width 16 of the separation chamber zone 7. In further illustrative embodiments, the function by which the widths of the plurality of channels 12 increases is a quadratic function. Accordingly, it will be appreciated that the channels can be characterized by significantly less amounts of variation among the widths than is schematically depicted in FIG. 7.

In general, each width 22a-g can be uniform or non-uniform across a length of the channel 12a-g. In the example embodiment of FIG. 7, each individual width 22a-g is substantially uniform across an entire length 23 of the channel 12a-g. The outlet ports 5 (e.g., at which the channels 12 terminate) similarly can have widths that vary from one another, as with the widths 22a-g of the channels 12a-g. For instance, the widths of the outlet ports 5 can be the same as the widths 22a-g of the channels 12a-g, and thus the widths of the outlet ports 5 can increase as a (e.g., quadratic) function of widthwise position relative to the center of the separation chamber zone 7. Alternatively, the widths of the outlet ports 5 can be different from the widths 22a-g of the channels 12a-g. In general, the widths of the outlet ports may be proportional or non-proportional to the widths 22a-g of the channels 12a-g.

In the example embodiment of FIG. 7, the micro-fluidic chamber 1 of the device includes the initial flow path deflector element 10 as well as the plurality of flow path deflector elements 11. In this example embodiment, the plurality of flow path deflector elements 11 are spaced apart at non-uniform distances, and the plurality of channels 12a-g are spaced apart at uniform distances. Accordingly, the non-uniform spacing of the plurality of flow path deflector elements 11 and the non-uniform widths 22a-g of the plurality of channels 12a-g (i.e., non-uniform across the plurality) can work in combination to maintain flow through the separation chamber 7 in a substantially parallel manner preventing lateral intermixing.

In general, the flow path deflector elements that are included in the device (e.g., the initial flow path deflector element 10 and/or the plurality of additional flow path deflector elements 11) can be any suitable physical structure for being positioned in such a way as to block the flow path of a sample of analytes and to thereby cause redirection of the sample upon impact of the sample against the flow path deflector elements 10, 11. For instance, in the example embodiments depicted and described with reference to FIGS. 1 through 7, the flow path deflector elements 10, 11 are pins (e.g., cylindrical columns), e.g., constructed of silicone or any other suitable material. However, it should be appreciated that many other shapes and configurations are possible and contemplated within the scope of the present disclosure.

Figure 8:
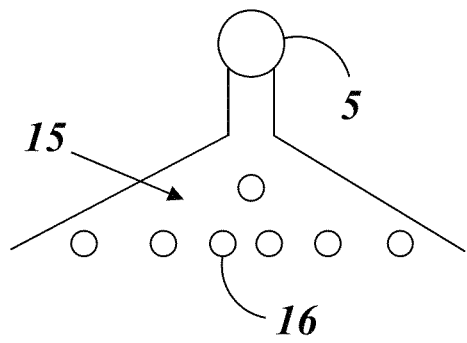
FIG. 8 depicts example embodiments of flow path deflector elements for inclusion in embodiments disclosed herein.
Figure 8:
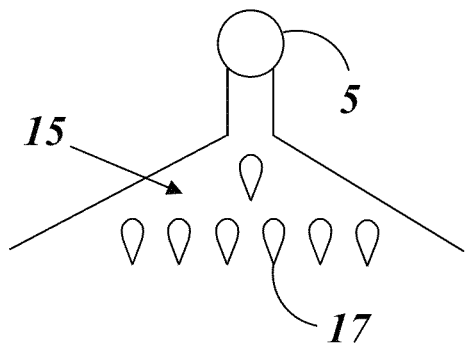
Figure 8:
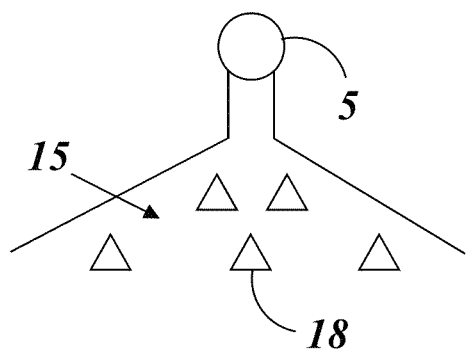
Figure 8:
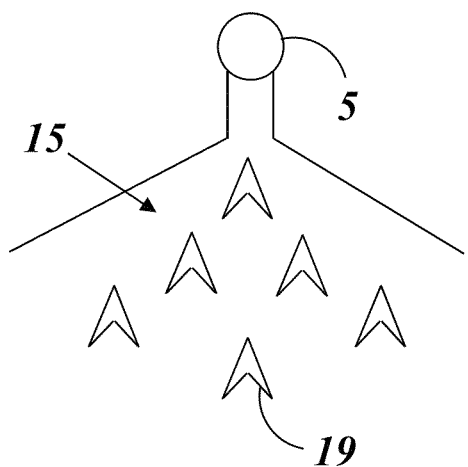
Figure 8:
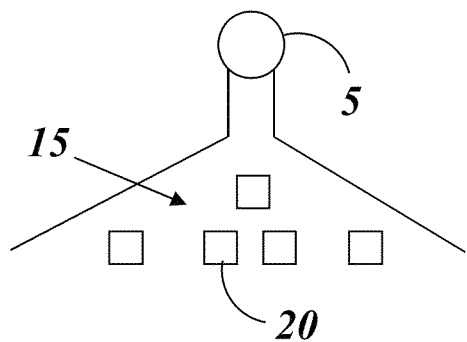
Figure 8:
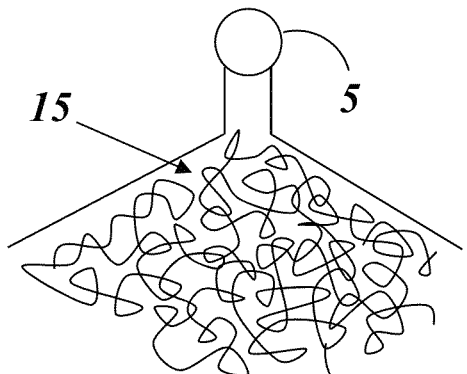

For instance, FIG. 8 illustrates several example embodiments of the flow path deflector elements 10, 11 from a top view. As illustrated, the flow path deflector elements 10, 11 can include one or more of a cylindrical column 16, a foil shaped member 17 (e.g., a fin, which can have a elliptical cross section when viewed from a front view), a triangular prism 18, a v-shaped column 19, a rectangular prism 20, a thicket 21 (e.g., steel wool or other material forming a tortuous path within the fluid distribution chamber zone 15), any other flow path deflector elements, and any suitable combination thereof. In embodiments including a thicket 21, the thicket 21 can fill at least a portion, only a portion, or substantially all of the fluid distribution chamber zone 15.

Figure 9:
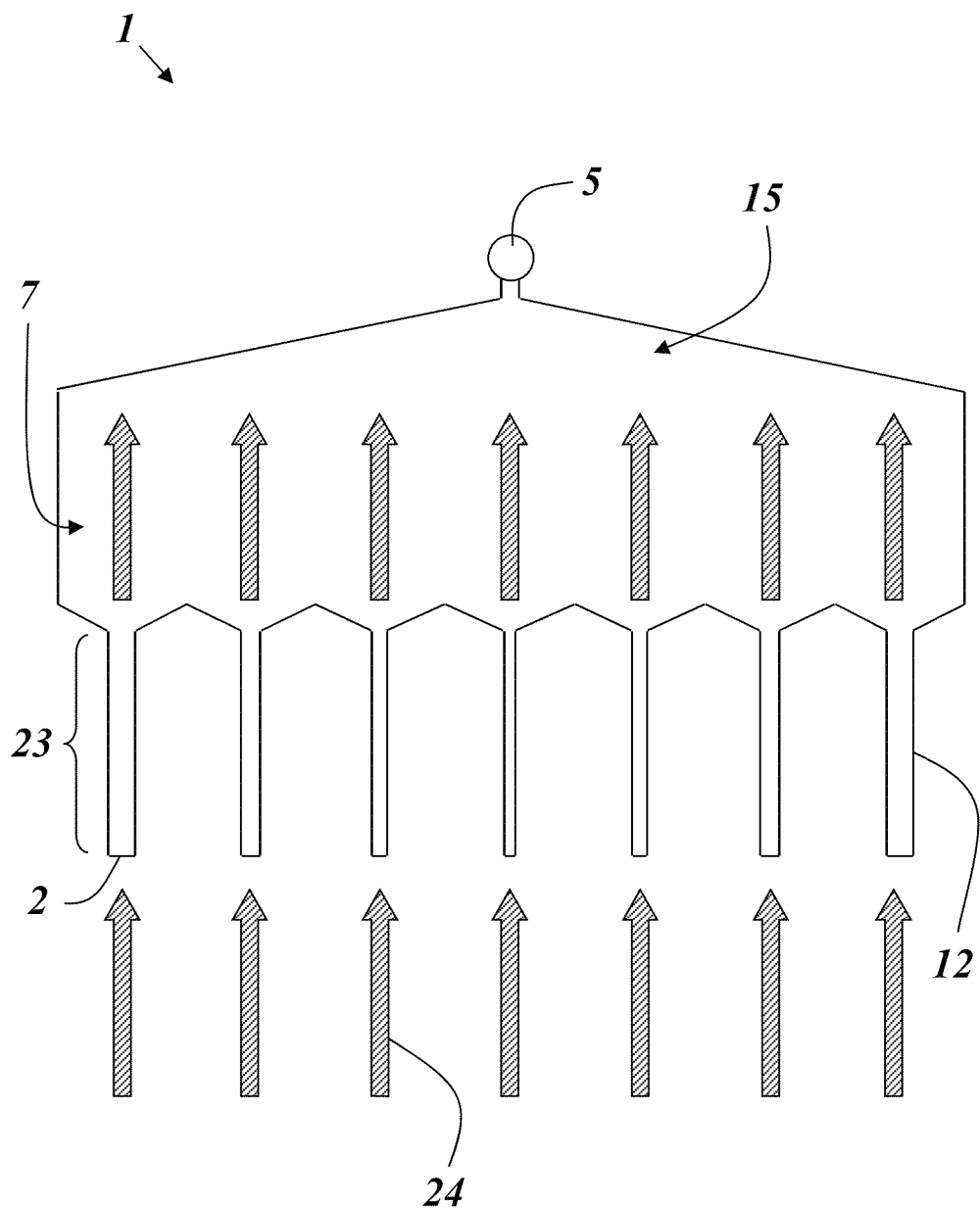
FIG. 9 depicts an example embodiment of a micro-fluidic chamber of a micro-fluidic device that does not include one or more flow path deflector elements.

Although the example embodiments of FIGS. 1 through 8 depict one or more flow path deflector elements (e.g., 10, 11), it should be appreciated that in some alternative embodiments, flow path deflector elements are not included. For instance, FIG. 9 depicts an example embodiment of a micro-fluidic chamber 1 for inclusion in devices provided herein. The micro-fluidic chamber 1 can include channels 12 having widths that are non-uniform across all of the channels 12, as depicted. Alternatively, the widths can be uniform across all of the channels 12. In embodiments such as the one depicted in FIG. 9, sample can be introduced into the separation chamber zone 7 in an evenly distributed fashion by drawing sample in through the outlet ports 2, e.g., as an alternative to introducing sample through the inlet port 5. Furthermore, in such embodiments, the lengths of the channels 12 can be significantly reduced, as would be appreciated by one of skill in the art upon reading the present specification.

Figure 10:
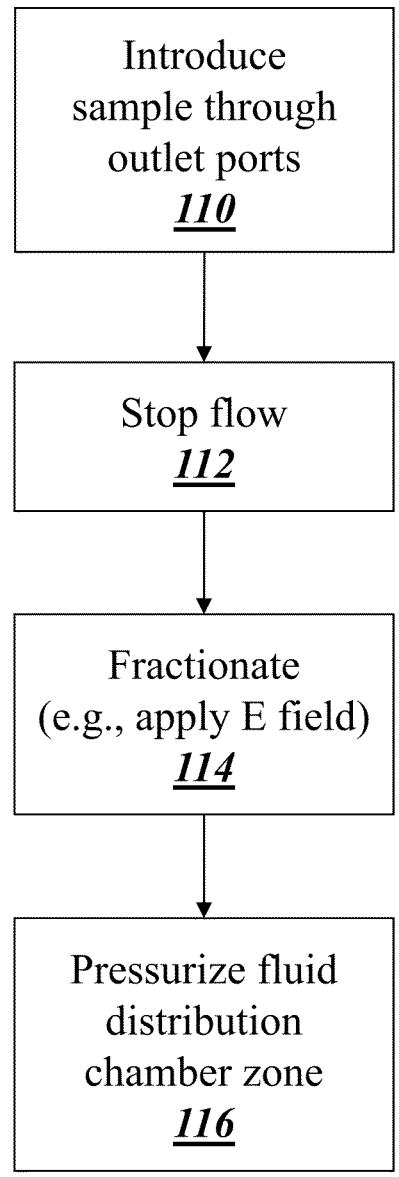
FIG. 10 depicts a flow chart of an example method for fractionating a sample by introducing the sample through a plurality of outlet ports.

For example, FIG. 10 depicts a flow chart of a method for using the device of FIG. 9 in order to fractionate a sample of analytes. Sample is introduced into the separation chamber zone 7 in an evenly distributed fashion through the outlet ports (step 110). More specifically, in illustrative embodiments, sample is drawn through each of the outlet ports 2, through each of the channels 12, and into a plurality of different widthwise positions in the separation chamber zone 7. For instance, sample can be introduced by producing a negative pressure at the inlet port 5. In some embodiments, the negative pressure at the inlet port 5 is produced by actuating a syringe, pipette, or other micro-pump coupled to the inlet port 5, which thereby causes the sample to flow into the outlet ports 2 from a fluid reservoir that is coupled to the outlet ports 2. As an alternative, in some embodiments, sample may be caused to be introduced through the outlet ports 2 by generating a positive pressure at the outlet ports 2.

Once sample is situated suitably within the separation chamber zone 7, flow preferably is stopped (step 112), e.g., by halting actuating motion of the syringe, pipette, or other micro-pump producing the negative pressure at the inlet port 5. The evenly distributed sample can be fractionated (step 114), e.g., by generating an electric field across the width 16 of the separation chamber zone 7. In this manner, a plurality of fractionated analyte groups can be generated after a sufficient period of time has passed. Once fractionated, the fluid distribution chamber zone 15 can be pressurized to force the fractionated analyte groups out through the channels 12 and outlet ports 2. For example, in illustrative embodiments, additional fluid (e.g., one or more gases, one or more liquids, or a combination thereof) is introduced through the inlet port 5 into the fluid distribution chamber zone 15, in such a way as to force the fractionated analyte groups back out through the outlet ports 5.

Preferably, additional fluid that is introduced into the fluid distribution chamber zone 15 to force fractionated analyte groups out the outlet ports 5 is less viscous than each of the plurality of fractionated analyte groups. When such additional, less viscous fluid is introduced into the fluid distribution chamber zone 15, it contacts the boundary of the fractionated analyte groups and distributes within the fluid distribution chamber zone 15. Once a sufficient quantity of the additional, less viscous fluid has passed through the inlet port 5, the additional fluid will compress until it possesses a great enough pressure to push the fractionated analyte groups through the channels 12 and out the outlet ports 5. Given that the additional, less viscous fluid distributes evenly throughout the fluid distribution chamber zone 15 prior to undergoing sufficient compression to build up a motive force, the pressure generated thereby is substantially evenly distributed along the entire width 16 of the separation chamber zone 7 (e.g., along the entire rearward boundary of the fractionated analyte groups). This even distribution of the additional, less viscous fluid causes the fractionated analyte group to flow back through the separation chamber zone 7 in a substantially parallel fashion, thereby preventing substantially lateral intermixing of the fractionated analyte groups.

Alternatively or additionally to utilizing an additional (e.g., less viscous) fluid, other methods of pressurizing the fluid distribution chamber zone 15 can be used in step 116. Furthermore, in embodiments where additional fluid is introduced in step 116, it is possible to utilize a more viscous or equally viscous fluid, e.g., by including the flow path deflector elements 10, 11 within the fluid distribution chamber zone 15 in a manner sufficient to cause even distribution of the additional fluid therein prior to contacting the fractionated analyte groups.

Figure 11A:
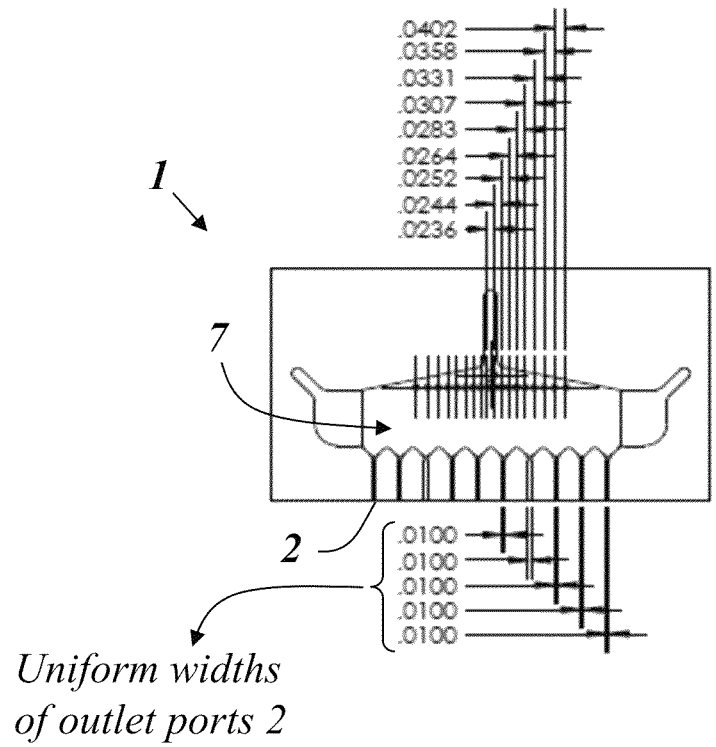
FIGS. 11A and 11B depict a top view and a front view, respectively, of an example alternative embodiment of a micro-fluidic chamber of a micro-fluidic device that includes one or more depth-variable channels.
Figure 11B:
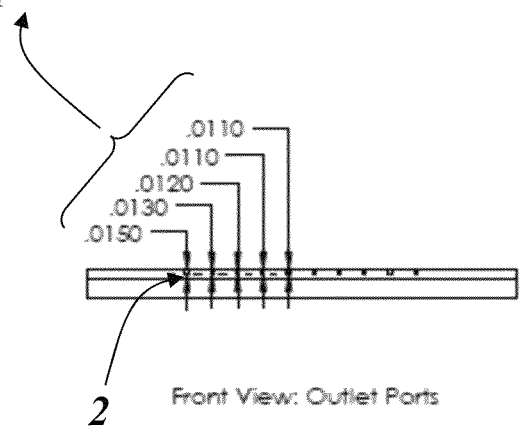

Still other alternative embodiments are possible. For example, one of skill in the art will appreciate upon reading the present specification that there are other ways to shape the outlet ports 2 such that outlet ports 2 having widthwise positions aligned nearer to the center of the width 16 of the separation chamber zone 7 are more restrictive to flow than outlet ports 2 having widthwise positions aligned nearer to the edges of the width 16 of the separation chamber zone 7. For instance, FIGS. 11A and 11B depict one such example of such a micro-fluidic chamber 1 of a micro-fluidic device from a top view and a front view, respectively. In particular, in the example embodiment of FIGS. 11A and 11B, depths (e.g., heights, as depicted in the front view of FIG. 11B) of the outlet ports 2 can be variable. The variable depths can be provided as an alternative or addition to providing the outlet ports 2 with variables widths, as depicted at least in FIGS. 7 and 9. In the example embodiment of FIGS. 11A and 11B, the widths are constant. All values in FIGS. 11A and 11B (which are in inches) are illustrative and in no way limit the embodiments provided herein.

One of skill in the art will appreciate that there are many ways to provide the outlet ports 2 with variable areas achieving the effect of greater flow restriction at widthwise positions nearer the center of the width 16 of the separation chamber zone 7.

Numerous modifications and alternative embodiments of the embodiments disclosed herein will be apparent to those of skill in the art in view of the foregoing description. Accordingly, this description is to be construed as illustrative only and is for the purpose of teaching those skilled in the art the best mode. Details of the structure may vary substantially without departing from the spirit of the embodiments provided here, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween. The publications, websites and other reference materials referenced herein to describe the background of the invention and to provide additional detail regarding its practice are hereby incorporated by reference.

EXAMPLES

Example 1

Dry Device Assembly

The devices as depicted in FIGS. 1 and 2 were fabricated as follows. The micro-fluidic channels (1) were cast in silicone (Elastosil® LR 3003/20, Wacker Chemical Corporation, Adrian, Mich.), allowed to set, but were not cured at elevated temperature. The separation zones (7) of these devices were about 20 mm by 5 mm, with a depth of about 0.5 mm. Flow distribution elements (11) were an array of eighteen 0.5 mm diameter posts, quadratically spaced over a 12 mm span. The glass lid (3) was mated to the silicone micro-fluidic channels (1) assuring proper alignment of the access ports (4, 5 and 6). Adhesion of the glass to the silicone was accomplished under mild clamping pressure, and curing the assembly at about 190° C. for 1 hour.

The assembled device was measured to have a separation zone (7) volume of about 70 µL. About 10 µL was required to fill the device up to the flow distribution chamber (15), and about 5 µL occupied all of the exit channels (12). Therefore, the total fluid occupied in the device was about 85 µL. The electrode gel pads (8 and 9) were each measured to have a volume of about 7.5 µL.

Example 2

Electrode Gels

The electrode gels (8 and 9) were created as 2% agarose (agarose low EEO, type I, Sigma-Aldrich Co. LLC, St. Louis, Mo.). A 2% agarose solution was created by dissolving the appropriate amount of agarose in a 20 mM, pH 7.2 phosphate buffer at about 90° C. A dry device assembled in accordance with Example 1 was heated to 60° C. in order to maintain the fluidity of the agarose solution. A 7.5 µL volume was pipetted into each electrode port. The device was cooled to room temperature, and the electrode gels were allowed to set. Platinum wires were inserted into each electrode gel to facilitate connection to a power supply.

Example 3

Running an Indicator Dye

A running buffer of 1 mM glutamic acid/1 mM histidine/1 mM lysine/2 mM, pH 7.2 phosphate buffer (all chemicals from Sigma-Aldrich Co. LLC, St. Louis, Mo.) was prepared. 7.5 µL of a saturated congo red solution was added to 150 µL of the running buffer. 80 µL of the congo red/running buffer mixture was introduced through the inlet port (5) into a device made in accordance with Example 2. The device was connected to an electrophoresis power supply (model EV215, Consort bvba, Turnhout, Belgium) and run at 50 VDC for 6 minutes.

The initial current drawn by the device was 107 µA. The red color was observed to move from the cathode gel almost immediately, indicating migration of the congo red toward the anode. At the interface between the running buffer and the anode gel, blue material started to form, indicating a drop of the pH at the anode and the alignment of the running buffer components in the electric field. The blue color propagated across the separation chamber, as the clear zone at the cathode end grew. After about 4 minutes of running, the blue region reached about 8 mm across the separation chamber, and there were no traces of red color left. This indicates migration of the congo red toward the anode and a pH of less than about 3.0 in the anode region of the device (congo red has a blue-red transition in a pH range of 3.0-5.2). After 6 minutes, the ending current was 172 µA. No disrupting eddy currents due to electroosmotic flow (EOF) were observed.

Example 4

Running Phycocyannin

A device was assembled in accordance with Example 2, except the electrode gels were set at different pHs to facilitate the formation of a pH gradient. The anode gel was made as a 1.5% agarose gel in 30 mM glutamic acid. The cathode gel was made as a 1.5% agarose gel in 30 mM lysine. Phycocyannin was run in a carrier ampholyte running buffer. Native phycocyannin (Sigma-Aldrich item P-2172) was dissolved in a 2% carrier pH 3-10 ampholyte solution (Sigma-Aldrich item 39878). The device was run at 120 VDC for 1 hour.

The initial current drawn by the system was about 130 µA (about 15 mW). The phycocyannin was observed to form a band within about 5 minutes near the anode end of the separation chamber. The band migrated to about 4 mm from the anode gel within 20 minutes of running, and remained stationary for the remainder of the run. The current drawn by the system was about 550 (6.6 mW) from about 4 minutes to the end of the run.

Example 5

Verification of Parallel Flow

A device, as described in Example 1, was filled with water containing a blue food coloring. Approximately 40 µL of water containing yellow food coloring was slowly introduced through the inlet port. A substantially straight blue-yellow boundary was observed in the middle of the separation chamber, thereby verifying parallel flow.

What is claimed is:

1. A micro-fluidic device for fractionating a sample of analytes according to their isoelectric points, the device comprising:
    a micro-fluidic chamber comprising one or more walls and a separation chamber zone contained within the one or more walls;
    an inlet port situated at a first end of the micro-fluidic chamber for introducing a sample of analytes into the separation chamber zone;
    a plurality of outlet ports situated at a second end of the micro-fluidic chamber substantially opposite the first end, the plurality of outlet ports extending across a width that is equal to at least part of a width of the separation chamber zone;
    a plurality of channels each leading from a different widthwise position in the separation chamber zone to one of the plurality of outlet ports; and
    one or more flow path deflector elements situated proximate the inlet port and situated between the inlet port and the plurality of outlet ports, the one or more flow path deflector elements being situated entirely in one or more positions preceding the separation chamber zone;
    wherein the one or more flow path deflector elements are positioned in such a way as to prevent substantial lateral intermixing of a plurality of fractionated analyte group as the plurality of fractionated analyte groups flows from one or more positions in the separation chamber zone to the plurality of channels.

2. The device of claim 1, further wherein at least one of the one or more flow path deflector elements block a shortest path between the inlet port and each of the plurality of outlet ports.

3. The device of claim 1, further comprising, for at least one of the plurality of channels, a pair of substantially opposing walls leading to the at least one of the plurality of channels, wherein the pair of substantially opposing walls narrows in a direction leading to the at least one of the plurality of channels.

4. The device of claim 1, further comprising, for each channel of the plurality of channels, two or more walls forming a bottleneck in a direction leading from the separation chamber zone to the channel.

5. The device of claim 1, further comprising a plurality of buffer components situated in the separation chamber zone in such a way as to enable a pH gradient to form within the separation chamber zone in the presence of an electric field.

6. The device of claim 1, further comprising an electric field generation device configured to generate an electric field having a direction extending across a width that is equal to at least part of the width of the separation chamber zone.

7. The device of claim 1, wherein the one or more flow path deflector elements comprise a plurality a flow path deflector elements extending across a width that is equal to at least part of the width of the separation chamber zone.

8. The device of claim 1, wherein the one or more flow path deflector elements comprises an initial flow path deflector element and a plurality of additional flow path deflector elements, wherein the initial flow path deflector element is situated between the inlet port and the plurality of additional flow path deflector elements, and wherein the plurality of additional flow path deflector elements are situated between the initial flow path deflector element and the plurality of outlet ports, the initial flow path deflector element blocking a shortest path between the inlet port and the plurality of outlet ports.

9. The device of claim 1, wherein the plurality of channels have widths that decrease moving from a widthwise position aligned with either edge of a width of the separation chamber zone to a widthwise position aligned with a center of the width of the separation chamber zone.

10. The device of claim 1, wherein the plurality of outlet ports have areas that decrease moving from a widthwise position aligned with either edge of a width of the separation chamber zone to a widthwise position aligned with a center of the width of the separation chamber zone.

11. The device of claim 1, wherein widths of the plurality of channels increase as a function of widthwise position relative to a center of a width of the separation chamber zone.

12. The device of claim 11, further wherein the function with which the widths of the plurality of channels increase is a quadratic function.

13. A method for isoelectrically fractionating a sample of analytes, comprising:
introducing the sample into a separation chamber zone through an inlet port situated on a first end of the micro-fluidic chamber;
causing the sample to flow through part of the separation chamber zone and impact one or more flow path deflector elements situated proximate the inlet port and situated between the inlet port and a plurality of outlet ports, at least one of the one or more flow path deflector elements blocking a shortest path between the inlet port and at least one of the plurality of outlet ports, whereby the sample is redirected upon impacting the one or more path deflector elements;
halting flow of the sample while the sample is in the separation chamber zone and isoelectrically fractionating the halted sample into a plurality of fractionated analyte groups;
causing the plurality of fractionated analyte groups to flow through a remainder of the separation chamber zone and through a plurality of channels each leading from a different widthwise position in the separation chamber zone to one of the plurality of outlet ports; and
causing the plurality of fractionated analyte groups to flow through the plurality of outlet ports, the plurality of outlet ports being situated at a second end of the micro-fluidic chamber substantially opposite the first end of the micro-fluidic chamber.

14. The method of claim 13, wherein the plurality of fractionated analyte groups do not substantially laterally intermix as the plurality of fractionated analyte groups flow from the separation chamber zone to the plurality of channels.

15. The method of claim 13, wherein the step of causing the plurality of fractionated analyte groups to flow through a remainder of the separation chamber zone and through a plurality of channels further comprises causing the plurality of fractionated analyte groups to flow past a plurality of pairs of substantially opposing walls each leading to one of the plurality of channels, wherein each of the plurality of pairs of substantially opposing walls narrows in a direction leading to the plurality of channels.

16. The method of claim 13, wherein each of the plurality of fractionated analyte groups has a different range of isoelectric points.

17. The method of claim 16, wherein the ranges of isoelectric points of the plurality of fractionated analyte groups are overlapping or non-overlapping.

18. The method of claim 13, wherein the step of causing the sample to impact one or more flow path deflector elements comprises causing the sample to impact an initial flow path deflector element and a plurality of additional flow path deflector elements, wherein the initial flow path deflector element is situated between the inlet port and the plurality of additional flow path deflector elements, and wherein the plurality of additional flow path deflector elements are situated between the initial flow path deflector element and the plurality of outlet ports, the initial flow path deflector element blocking a shortest path between the inlet port and the plurality of outlet ports.

19. The method of claim 13, wherein the plurality of channels have widths that decrease moving from a widthwise position aligned with either edge of a width of the separation chamber zone to a widthwise position aligned with a center of the width of the separation chamber zone.

20. The method of claim 13, wherein widths of the plurality of channels increase as a function of widthwise position relative to a center of a width of the separation chamber zone.

21. The method of claim 20, further wherein the function with which the widths of the plurality of channels increase is a quadratic function.

22. A micro-fluidic device for fractionating a sample of analytes according to their isoelectric points, the device comprising:
a micro-fluidic chamber comprising one or more walls, a separation chamber zone contained within the one or more walls, and a fluid distribution chamber zone contained within the one or more walls and situated in such a way as to precede the separation chamber zone;
an inlet port situated at a first end of the micro-fluidic chamber for passing a sample of analytes into the separation chamber zone;
a plurality of outlet ports situated at a second end of the micro-fluidic chamber substantially opposite the first end, the plurality of outlet ports extending across a width that is equal to at least part of a width of the separation chamber zone;
a plurality of channels each leading from a different widthwise position in the separation chamber zone to one of the plurality of outlet ports;
a first flow path redirection element situated outside the separation chamber zone proximate the inlet port and situated between the inlet port and the plurality of outlet ports; and
a plurality of additional flow path redirection elements situated entirely outside the separation in the fluid distribution chamber zone proximate the first flow path redirection element and situated between the first flow path redirection element and the plurality of outlet ports;

wherein the first flow path redirection element and the plurality of additional flow path redirection elements are positioned in such a way as to substantially prevent lateral intermixing of a sample of analytes flow through the separation chamber zone and out of the plurality of outlet ports.

23. A micro-fluidic device for fractionating a sample of analytes according to their isoelectric points, the device comprising:

a pipette coupled to a micro-fluidic chamber comprising one or more walls and a separation chamber zone contained within the one or more walls;

an inlet port situated at a first end of the micro-fluidic chamber for introducing a sample of analytes from the pipette into the separation chamber zone;

a plurality of outlet ports situated at a second end of the micro-fluidic chamber substantially opposite the first end, the plurality of outlet ports extending across a width that is equal to at least part of a width of the separation chamber zone;

a plurality of channels each leading from a different widthwise position in the separation chamber zone to one of the plurality of outlet ports; and one or more flow path deflector elements situated outside the separation chamber zone and proximate the inlet port and situated between the inlet port and the plurality of outlet ports, at least one of the one or more flow path deflector elements blocking a shortest path between the inlet port and at least one of the plurality of outlet ports.

24. A method for isoelectrically fractionating a sample of analytes, comprising:

causing a sample to flow through a plurality of first ports situated on a first end of a micro-fluidic chamber and into a separation chamber zone contained within the micro-fluidic chamber by applying a negative pressure at a second port situated at a second end of the micro-fluidic chamber that is substantially opposite the first end, whereby the sample is caused to flow in a first direction;

halting flow of the sample once the sample is evenly distributed in the separation chamber zone and isoelectrically fractionating the halted sample into a plurality of fractionated analyte groups; and causing the plurality of fractionated analyte groups to flow through the separation chamber zone and out the plurality of first ports, whereby the plurality of fractionated analyte groups are caused to flow in a second direction substantially opposite the first direction.

* * * * *

UNITED STATES PATENT AND TRADEMARK OFFICE
CERTIFICATE OF CORRECTION

PATENT NO. : 9,182,372 B2
APPLICATION NO. : 13/682430
DATED : November 10, 2015
INVENTOR(S) : Stephen G. Haralampu It is certified that error appears in the above-identified patent and that said Letters Patent is hereby corrected as shown below:

In the Claims:

Column 20, claim 1, line 52, the word "group" should read "groups".

Column 22, claim 22, line 67, through column 23, line 1, the phrase "outside the separation in the fluid distribution chamber" should read "outside the separation chamber".

Column 23, claim 22, line 7, the word "flow" should read "flowing".

Signed and Sealed this
Thirty-first Day of May, 2016

Michelle K. Lee
*Director of the United States Patent and Trademark Office*